(12) United States Patent
Carbone et al.

(10) Patent No.: US 11,324,884 B2
(45) Date of Patent: May 10, 2022

(54) DEVICE FOR INFUSION OF FLUIDS

(71) Applicant: GAMASTECH S.R.L., Sant'Agata Li Battiati CT (IT)

(72) Inventors: Domenico Carmelo Carbone, Catania (IT); Giuseppe Renato Massimo Recca, Catania (IT); Arturo Maravigna, Catania (IT)

(73) Assignee: GAMASTECH S.R.L., Sant'Agata Li Battiati CT (IT)

( * ) Notice: Subject to any disclaimer, the term of this patent is extended or adjusted under 35 U.S.C. 154(b) by 943 days.

(21) Appl. No.: 15/749,256

(22) PCT Filed: Jul. 20, 2016

(86) PCT No.: PCT/IB2016/054301
§ 371 (c)(1),
(2) Date: Jan. 31, 2018

(87) PCT Pub. No.: WO2017/025829
PCT Pub. Date: Feb. 16, 2017

(65) Prior Publication Data
US 2018/0221571 A1    Aug. 9, 2018

(30) Foreign Application Priority Data
Aug. 7, 2015    (IT) .................. 102015000043474

(51) Int. Cl.
*A61M 5/152*    (2006.01)
*A61M 5/148*    (2006.01)
(Continued)

(52) U.S. Cl.
CPC ............ *A61M 5/152* (2013.01); *A61M 5/145* (2013.01); *A61M 5/148* (2013.01); *A61M 5/1407* (2013.01); *A61M 2005/14506* (2013.01)

(58) Field of Classification Search
CPC ........ A61M 5/152; A61M 2005/14506; A61M 5/148; A61M 5/145; A61M 5/1483; A61M 5/1486; A61M 5/155; B65D 83/0061
See application file for complete search history.

(56) References Cited

U.S. PATENT DOCUMENTS

| | | | | |
|---|---|---|---|---|
| 4,187,847 A | * | 2/1980 | Loeser | A61M 5/16886 604/134 |
| 5,672,167 A | * | 9/1997 | Athayde | A61M 5/1483 604/892.1 |

(Continued)

FOREIGN PATENT DOCUMENTS

WO    2007075280 A1    7/2007

OTHER PUBLICATIONS

"Elastomeric." Merriam-Webster, Merriam-Webster, www.merriam-webster.com/dictionary/elastomeric. Date Accessed: Jan. 12, 2021 (Year: 2021).*

(Continued)

*Primary Examiner* — Emily L Schmidt
*Assistant Examiner* — Joshua Parker Reddington
(74) *Attorney, Agent, or Firm* — Lucas & Mercanti, LLP

(57) ABSTRACT

A device for infusion of medical fluids is provided. It has an internal reservoir for a fluid to be administered made of a first flexible base material to vary its volume as a function of the quantity of fluid present thereinside; and an outer casing containing the reservoir, having a side wall made of a second elastic base material suitable to make elastically deformable the casing to vary the geometry and internal volume thereof as a function of the volume of the reservoir.

7 Claims, 6 Drawing Sheets

(51) Int. Cl.
A61M 5/145 (2006.01)
A61M 5/14 (2006.01)

(56) References Cited

U.S. PATENT DOCUMENTS

| | | |
|---|---|---|
| 8,177,740 B1 | 5/2012 | McGlothlin et al. |
| 2005/0267422 A1 | 12/2005 | Kriesel |
| 2008/0077116 A1* | 3/2008 | Dailey .................... A61M 5/36 |
| | | 604/410 |
| 2008/0275422 A1* | 11/2008 | Ross .................. A61M 5/1483 |
| | | 604/408 |

OTHER PUBLICATIONS

Company, Houghton Mifflin Harcourt Publishing. "The American Heritage Dictionary Entry: Polyethylene." American Heritage Dictionary Entry: Polyethylene, www.ahdictionary.com/word/search.html?q=polyethylene. Date Accessed: Jan. 12, 2021 (Year: 2021).*
International Search Report and Written Opinion for International Application No. PCT/IB2016/054301 (9 Pages) (dated Nov. 14, 2016).

* cited by examiner

DEVICE FOR INFUSION OF FLUIDS

CROSS-REFERENCE TO RELATED APPLICATIONS

This application is a 371 of PCT/IB2016/054301, filed Jul. 20, 2016 which claims the benefit of Italian Patent Application No. 102015000043474, filed Aug. 7, 2015.

TECHNICAL FIELD OF THE INVENTION

The present invention can be applied in the field of the medical devices and it relates to a device for infusion of medical fluids.

BACKGROUND

As it is known, the devices for infusion of medical fluids by intravenous, intramuscular or subcutaneous routes, such as physiological or pharmacological solutions, are devices intended to be inserted inside a line for administering the fluid so as to favour the controlled and adjustable passage thereof from a container, such as a phial, bottle or the like, to an administering device such as a needle, a catheter or other known device to be inserted in the patient body for the fluid infusion.

An example of similar medical devices currently present on the market is represented by the elastomeric pumps, disposable devices the operation thereof is based upon the swelling of an elastomeric element which, thanks to the its mechanical properties, puts in pressure the fluid contained inside thereof.

Typically, the known elastomeric pumps comprise a reservoir made of elastomeric material housing the fluid to be administered and a protective outer casing including the reservoir.

The outer casing can be made both of rigid material and soft and flexible material to support the expansion and contraction motions of the reservoir.

The rigid outer casings mainly have the purpose of protecting the elastomeric reservoir, by avoiding that the same could be damaged by falls, accidental punctures or that in case of rupture thereof the fluid could be discharged in an uncontrolled manner, even though they allow a minimum discharge of the fluid thanks to the presence of a small hole necessary for the expansion and contraction motion.

The soft casings instead have the only function of protecting the elastomeric reservoir and they constitute a partial containment barrier in case of rupture of the reservoir. Even in this case a small hole is however present which would allow a minimum liquid discharge.

In any case, in the described solutions the outer casing, both a rigid or flexible casing, plays only a passive containment function of the reservoir and it does not participate actively to the administering phase.

Before using the pump, the elastomeric reservoir is filled up with a predetermined quantity of fluid so as to make it expand. In this way, the elastic return of the reservoir to the not deformed condition will produce the fluid supply, after a first priming phase adapted to the complete expulsion of the air existing in the whole infusion line.

Actually, the reservoir deformation due to the filling-in with the fluid generally takes place, apart from the elastic field, even at least partially in the plastic field.

Disadvantageously, the fact that the reservoir of the devices of known type deforms even plastically makes such devices likely to be used only once, and not more times. In fact, once deformed plastically, the reservoir has less capability of deforming elastically and then it allows to store a not always linear amount of deformation energy to be returned to the fluid, and so as to vary then the correct supply thereof.

Still, disadvantageously, the filling-in of the reservoir of the known devices of disposable type cannot be performed for too much time before using the device.

In fact, the stress of the reservoir by the fluid for prolonged time could lead to an excessive plastic deformation, which would not guarantee the fact of releasing on the fluid the energy required for the correct supply thereof during the use phase.

Furthermore, in order to replace an excessively deformed reservoir and to allow the re-use of the devices of known type, it is necessary to perform the procedures for opening the outer casing, decoupling the reservoir, extracting the reservoir, installing a new reservoir and at last closing the outer casing, which result to be unusable without invalidating the product sterility.

An additional drawback of the above-mentioned solutions is represented by the fact that the overall dimension volumes of the devices with rigid casing currently on the market on the average are larger by 50% than the maximum volume of included fluid, even under condition of empty reservoir.

Furthermore, generally, such devices are implemented according to axialsymmetric, for example cylindrical or spherical, configurations and consequently they result to be bulky and showy if applied on the patient.

An additional drawback is represented by the fact that the contact between the fluid and the elastomeric, generally silicone, material of the reservoir can alter the included solution in the average-long period.

SUMMARY OF THE INVENTION

The object of the present invention is to overcome the drawbacks mentioned above with reference to the known art.

Such problem is solved by a device for infusion of fluids according to claim 1.

Preferred features of the present invention are defined in the depending claims.

The present invention provides a device for infusion of fluids having features with high efficiency and reduced overall dimensions with respect to the devices of known type.

Advantageously, the fact of having particularly reduced overall dimensions allows to use the device even directly on the patient thereto the fluid is supplied, in a discrete way, while protecting the privacy thereof.

To this purpose, the device according to the present invention has an outer casing allowing a progressive reduction in the total overall dimensions of the device during infusion. The device in fact results to be particularly compact under condition of absent fluid.

A particular object of the invention is further to provide a highly ergonomic and relatively low cost device for infusion of fluids.

An additional advantage associated to the present invention is to provide a not necessarily disposable device for infusion of fluids, allowing quick and cheap maintenance or repair procedures.

The not last object is to implement a device for infusion of fluids avoiding the contact of fluid with materials which could potentially alter it, such as silicone materials.

Such objects, as well as other ones which will appear clearer hereinafter, are achieved by a device for infusion of fluids comprising an internal reservoir for a fluid to be administered, made of a first flexible base material to vary its volume as a function of the quantity of fluid present thereinside, said reservoir being fluidically connectable to a fluid infusion line.

The device further comprises an outer casing containing said reservoir, at least partially made of a second elastomeric base material suitable to make elastically deformable the casing to vary the geometry and internal volume thereof as a function of the volume of said reservoir.

Under the term "elastomeric" all materials, both synthetic and natural ones, are referred, characterized by a high elasticity and by the capability of returning, after being subjected to a deformation, to an original rest condition once the action which has caused the deformation thereof has ceased.

Examples of elastomeric materials with synthetic origin are those based upon butadiene-acrylonitrile, fluorinated, isoprene, propylene, and silicone elastomers. Among the natural elastomers natural rubber and caoutchouc can be used.

Thanks to this combination of features, the outer casing assumes its configuration of maximum overall dimensions only when the reservoir is filled up with the maximum possible quantity of fluid to be administered.

In fact, the filling-in with the fluid causes an increase in volume of the reservoir, which, in turn, causes an increase in volume of the outer elastic casing.

Correspondingly, after the fluid administration, the volume of the casing, and thus of the device, decreases proportionally to the volume of supplied fluid.

The presence of at least a portion made of elastomeric material makes that the casing has not exclusively the passive function of protecting the reservoir.

In fact, after having deformed elastically as a result of the reservoir filling-in, the elastic return of the casing to the original undeformed condition produces the action of a pressure on the reservoir and such pressure causes the fluid supply. In other words, the casing is active portion of the process for administering the fluid.

According to a preferred embodiment of the invention, the outer casing comprises a side wall made of the second base material, closed on the top and on the bottom by a pair of front walls made of a third rigid or semi-rigid base material.

In this way the casing, however, will have the function of protecting the reservoir, even thanks to the presence of a side wall which, even if it is made of preferably elastomeric material, will however guarantee sufficient protection for the reservoir from accidental punctures and impacts.

In a first variant, the first base material thereof the reservoir is made can be an elastomeric material selected from the group comprising the silicone materials and the like, so as to make reservoir active portion of the process for supplying the fluid.

In a second preferred variant, the reservoir is made of a thermoplastic material, free of silicone.

In this case, one avoids to put the fluid to be administered in contact with materials which could alter the composition thereof, but without damage as far as the action of administering the fluid is concerned, which as said in advance is exerted by the outer casing. To this purpose, it will be possible to divide the internal reservoir into two or more sections, preferably independent therebetween but connected to the same infusion line.

In this context, an additional application of embodiments of the device according to the present invention compatible with the medical fluids can be the use in replacement of the traditional drips.

As it is known, the drips require the force of gravity in order to be able to infuse medicinal substances, by involving a high position of the drip with respect to the infusion point.

In particular, the patients requiring infusions by drips, even if they are not confined to bed, are constrained at least to the presence of the drip stand, which causes considerable overall dimension and annoyance.

The drips, notwithstanding the described disadvantages, are used nowadays as they are able to be filled-in in advance by the pharmaceutical companies and they are able to infuse not stable medicinal substances not compatible with the currently on the market elastomeric devices.

On the contrary, the device of the invention, even if it can be filled-in in advance by the pharmaceutical company, does not require the drip stand or additional aids. Thus it can allow the patient to enjoy the required administration of medical fluid while avoiding excessive overall dimensions and not inserting limitations to the mobility thereof.

Other advantages, features and use modes of the present invention will result evident from the following detailed description of a preferred embodiment of the invention, shown by way of example and not for limitative purposes.

BRIEF DESCRIPTION OF THE FIGURES

The enclosed figures will be referred to, wherein.

The above-mentioned figures are to be meant exclusively by way of example and not for limitative purposes.

DETAILED DESCRIPTION OF PREFERRED EMBODIMENTS

By referring to the enclosed figures a preferred, but not exclusive, configuration of the device for infusion of fluids according to the present invention is illustrated, suitable to allow the administration of medical fluids inside the human body, for example by intravenous, intramuscular, subcutaneous route or the like.

The device could be used with any type of fluid or mixture of medical fluids, such as physiological or pharmacological solutions, without particular limitations.

Figure 1:
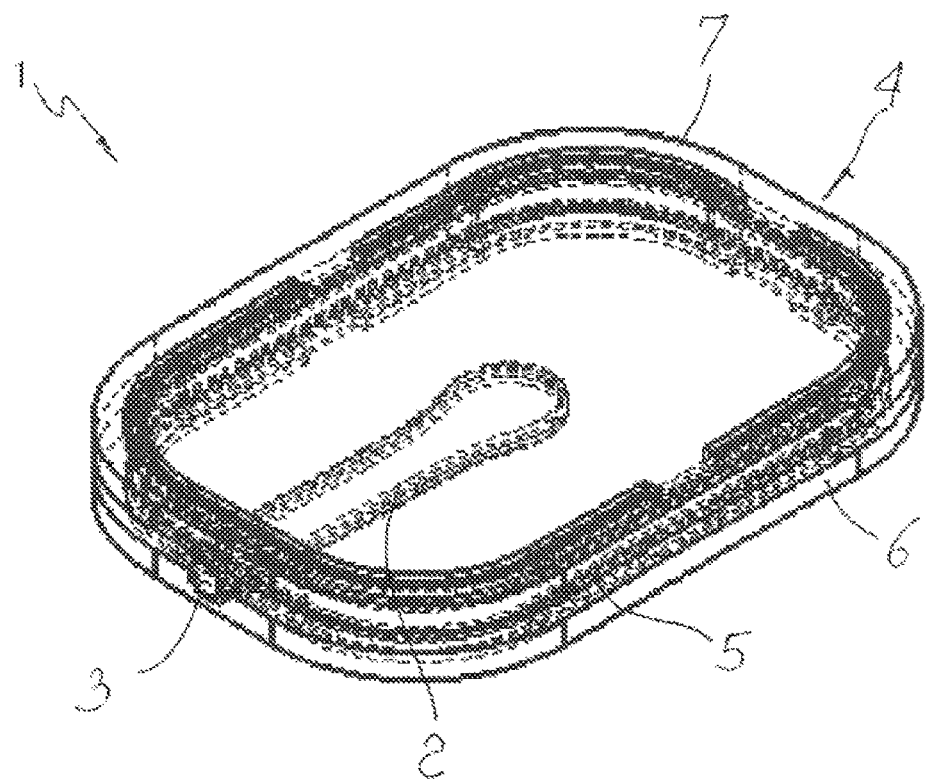
FIG. 1 is a perspective view of the device under a first undeformed condition in absence of fluid thereinside and wherein the not visible internal portions are illustrated with dash line.
Figure 2:
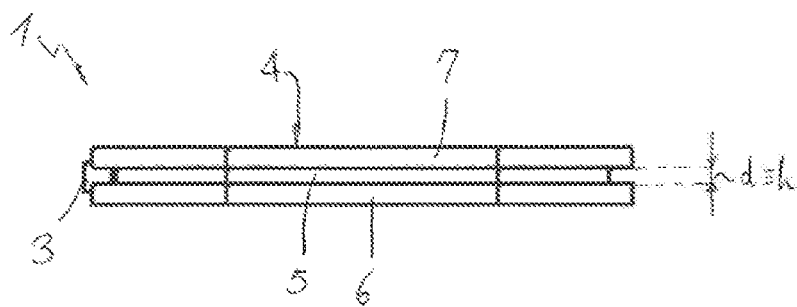
FIG. 2 is a side view of the device of FIG. 1.

FIG. 1 illustrates the device according to the invention, designated as a whole with 1, in an undeformed configuration of minimum overall dimensions corresponding to a condition of substantial absence of fluid, that is in a configuration preceding the filling-in or subsequent to the whole emptying thereof.

Figure 11:
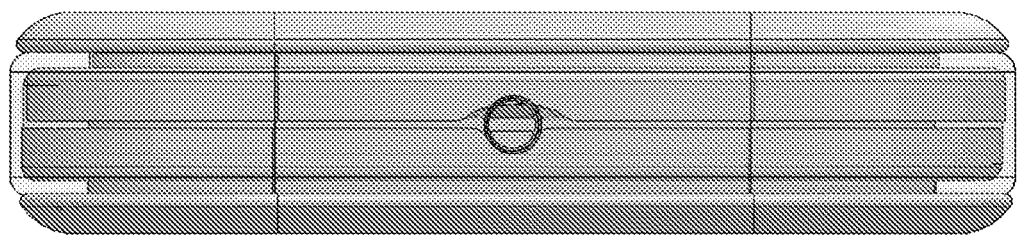
FIGS. 11 to 13 show a front, side and exploded view of the device of FIG. 1, respectively.
Figure 12:
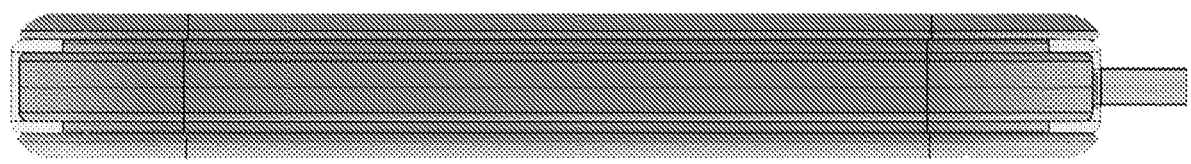
Figure 13:
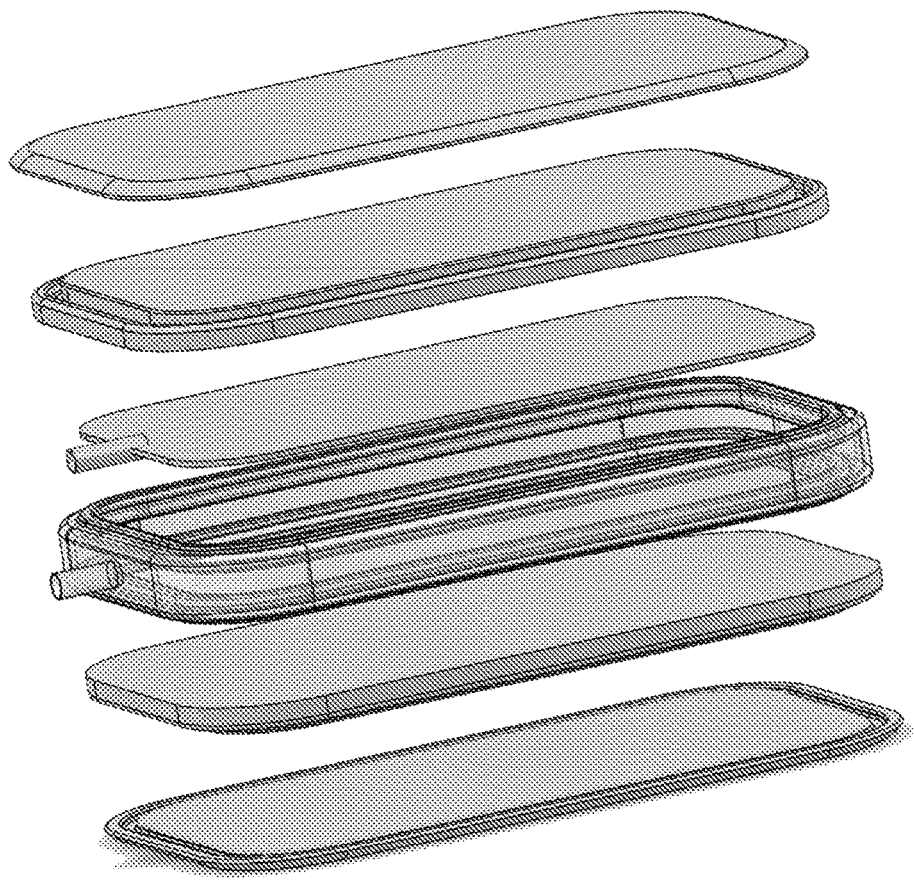
Figure 14:
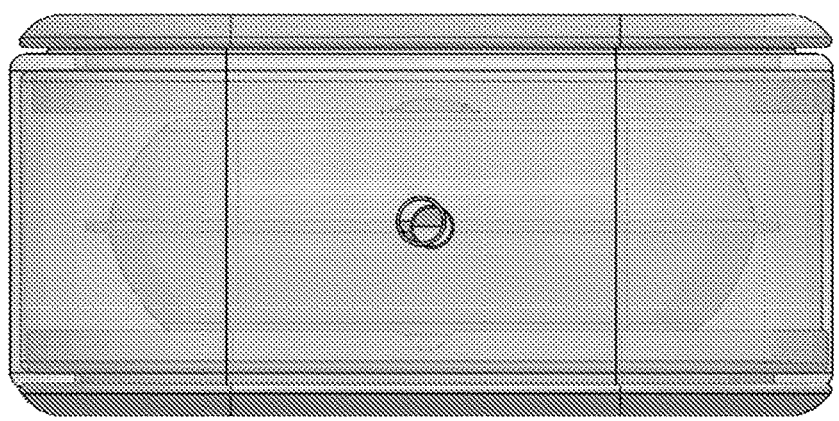
FIGS. 14 to 17 show a front, side, front perspective and exploded view of the device of FIG. 4, respectively.
Figure 15:
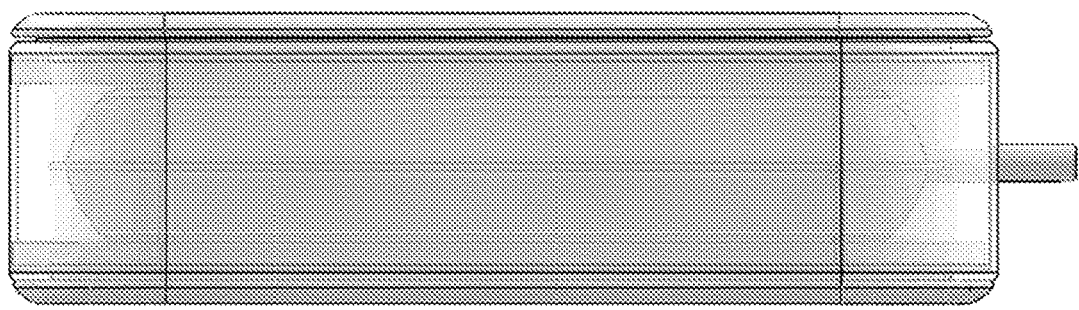
Figure 16:
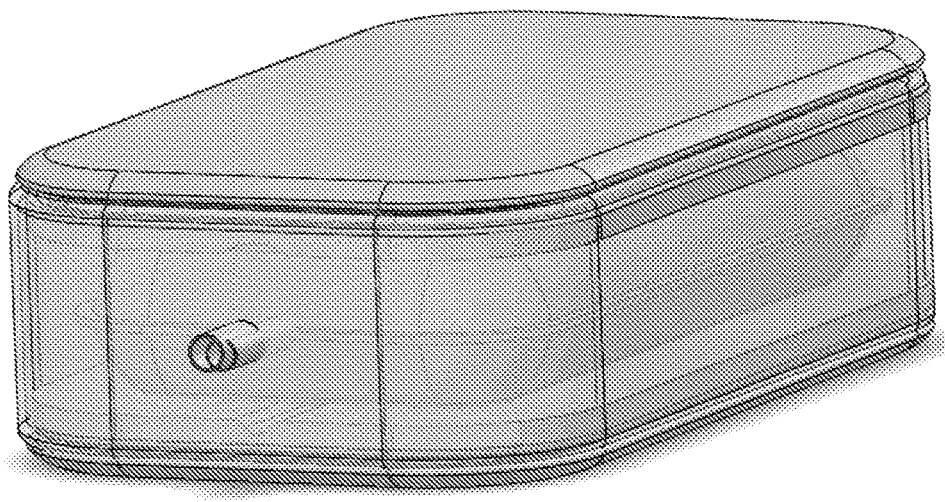
Figure 17:
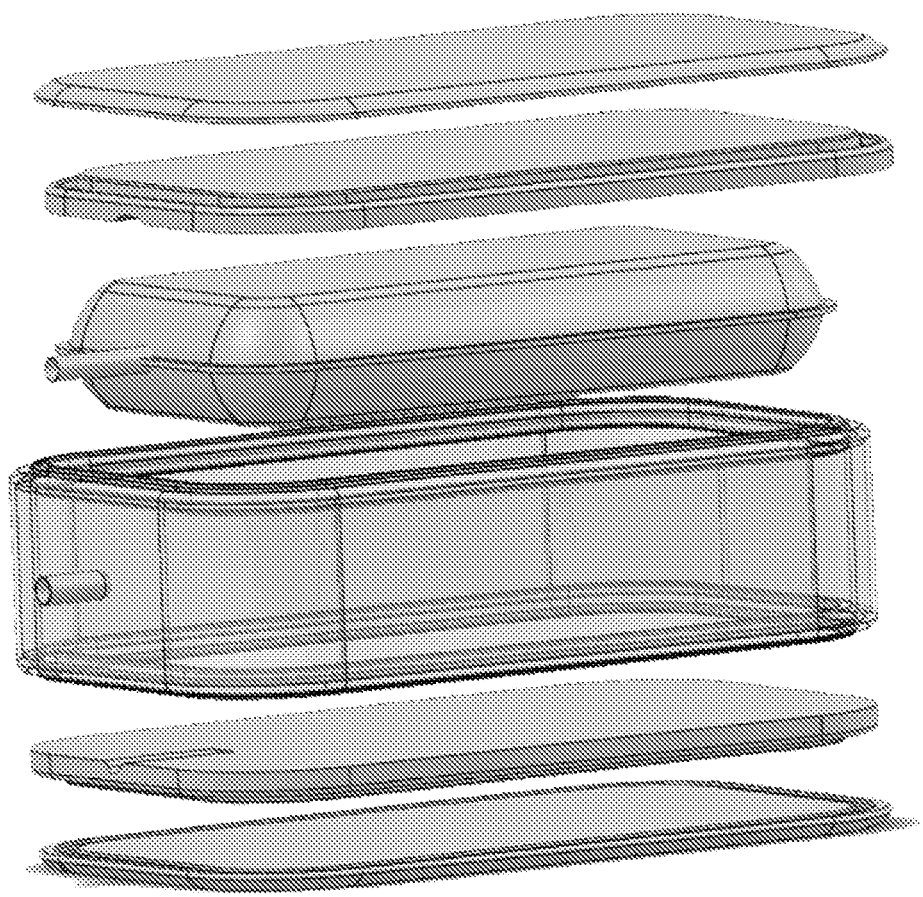

In order to improve understanding of the invention, additional exemplifying drawings of a preferred embodiment of the device according to the present invention in an undeformed configuration of minimum overall dimensions are shown in FIGS. 11 to 13.

Still by referring to FIG. 1, the device 1 comprises an internal reservoir 2, drawn with dash line, intended to include a predetermined and variable volume of the fluid to be administered. The reservoir 2 is made of a first flexible base material to vary the volume thereof as a function of the quantity of fluid introduced thereinside.

In typical way for this type of infusion devices, commonly defined also elastomeric pumps, the reservoir 2 has an opening 3 adapted to be fluidically connected to a standard infusion line, not illustrated as known, which can have also flow-regulating function.

According to preferred embodiments of the invention, the reservoir can be divided into two or more sections, preferably independent therebetween, and connected to the same infusion line.

The reservoir 2 is included inside an outer casing 4 having at least a portion made of a second elastic, preferably elastomeric, base material, adapted to make elastically deformable the casing 4.

The casing 4 having a minimum overall dimensions, under undeformed conditions, is considered substantially similar to the minimum overall dimensions of the reservoir 2 under conditions of absence of liquid thereinside.

In other words, in absence of liquid, the total overall dimensions of the device coincides with the minimum overall dimensions of the undeformed casing. Therefore, under this condition, the device results to be particularly compact.

By inserting the fluid inside the reservoir 2 an expansion thereof will be produced, and such increase in volume will cause the consequent elastic deformation of the casing 4 including it. The casing 4 will vary both the geometry and internal volume thereof as a function of the volume of the reservoir 2.

Figure 4:
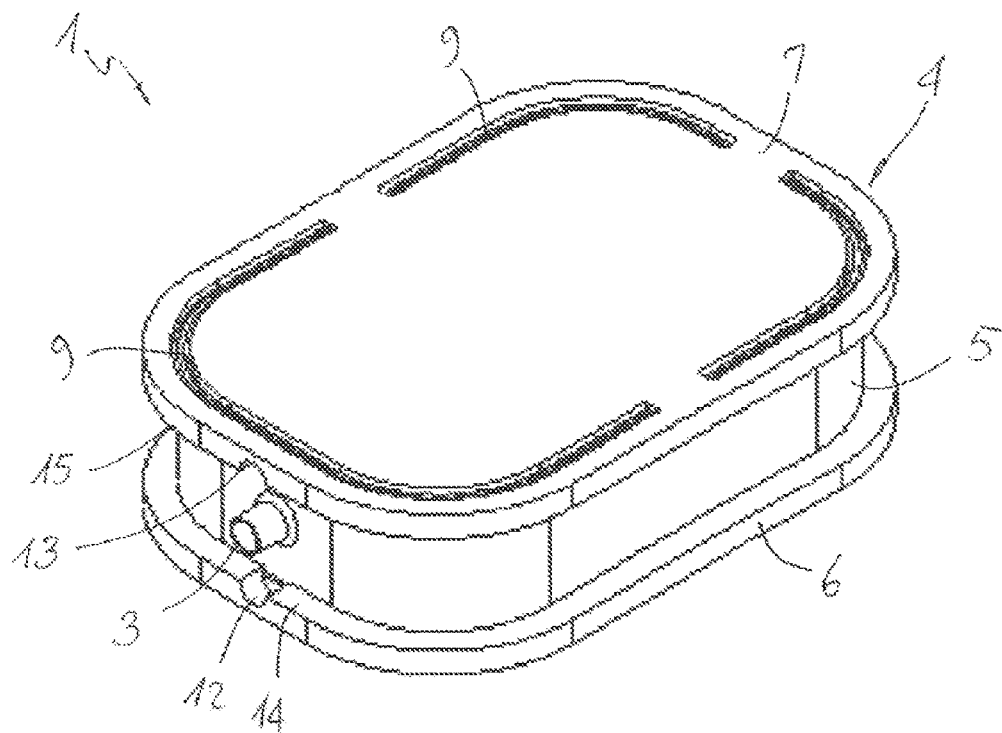
FIG. 4 is a perspective view of the device under a second deformed condition in presence of the maximum quantity of fluid thereinside.
Figure 5:
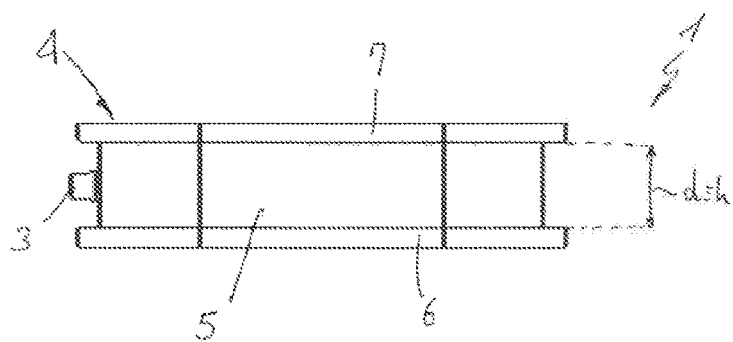
FIG. 5 is a side view of the device of FIG. 4.
Figure 6:
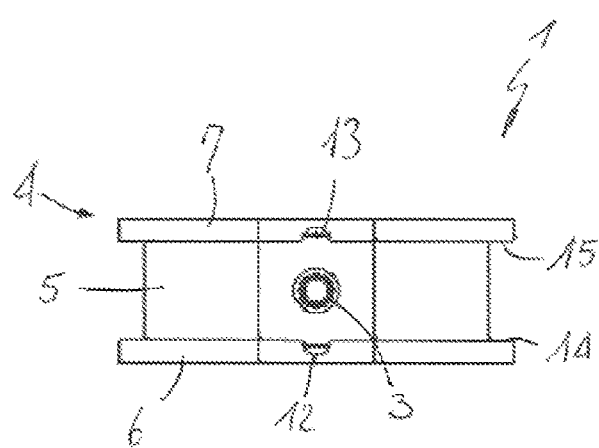
FIG. 6 is a front view of the device of FIG. 4.
Figure 7:
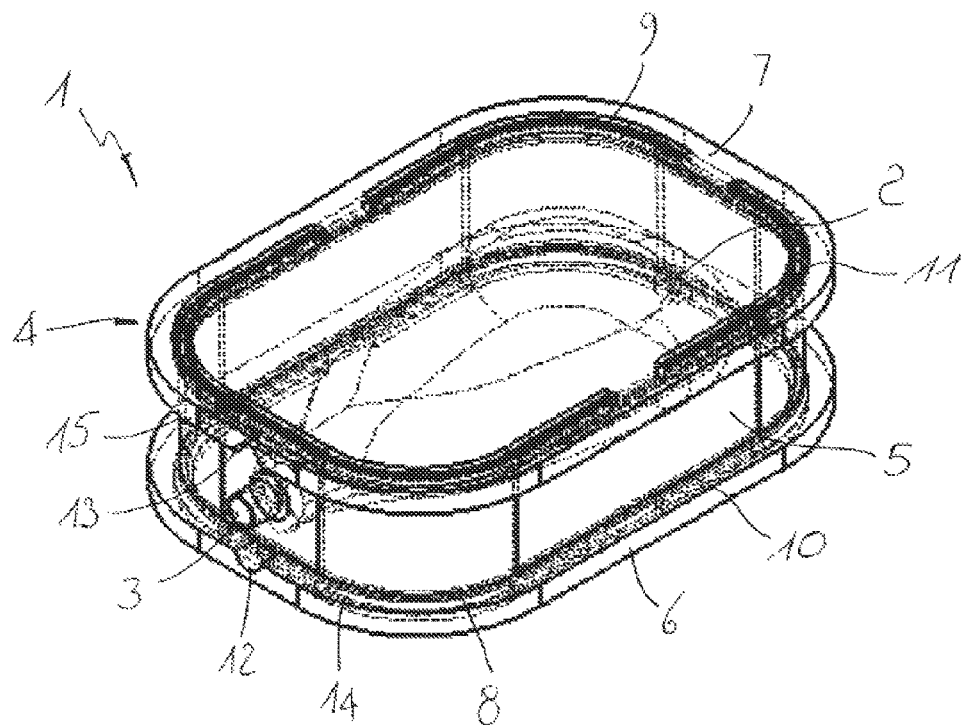
FIG. 7 is a perspective view of the device under the second deformed condition wherein the not visible internal portions are illustrated with dash line.
Figure 8:
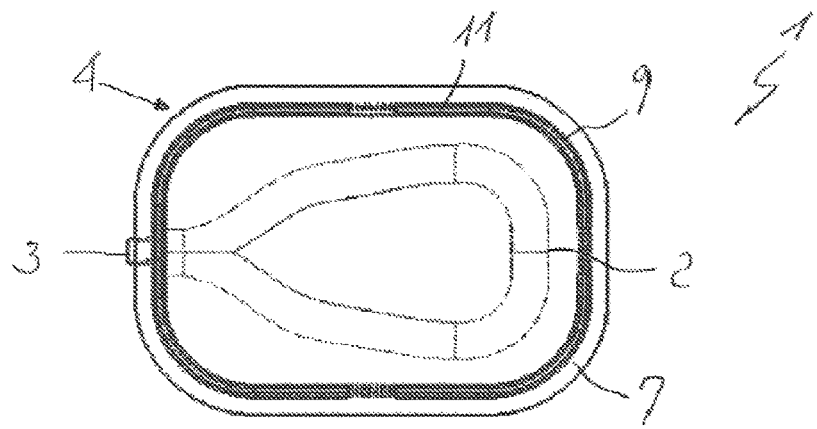
FIG. 8 is a top view of the device of FIG. 7.
Figure 9:
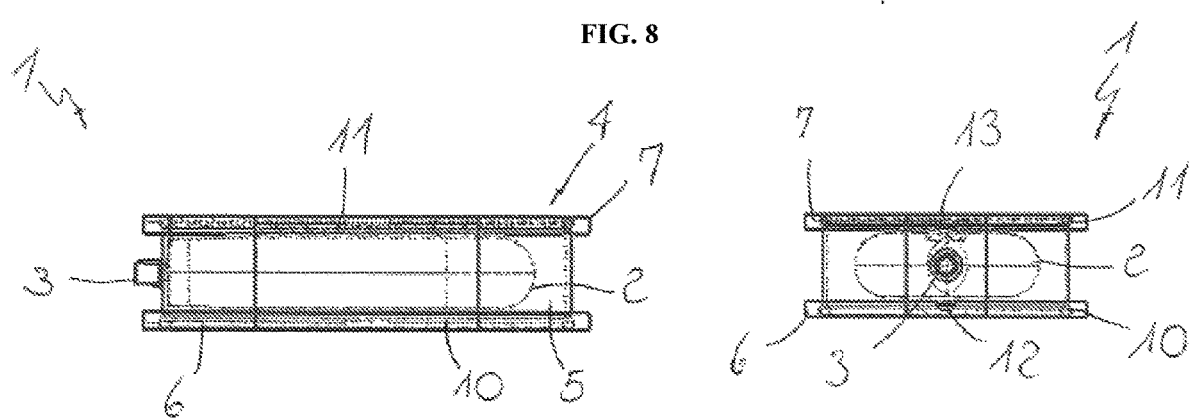
FIG. 9 is a side view of the device of FIG. 7.
Figure 10:
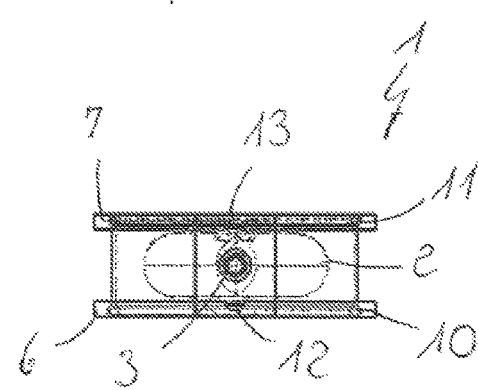
FIG. 10 is a front view of the device of FIG. 7.

FIG. 4 illustrates the device 1 in the configuration thereof of maximum volume, corresponding to the maximum volume of the outer casing 4 when inside the inner reservoir 2 the maximum quantity of fluid is included.

In order to improve understanding of the invention, additional drawings exemplifying a preferred embodiment of the device according to the present invention in a deformed configuration of maximum overall dimensions are shown in FIGS. 14 to 17.

In the preferred, but not exclusive, configuration, shown in the enclosed FIGS. 4 to 10—with particular reference to FIG. 4—the outer casing 4 comprises a side wall 5 made of the second base material with elastomeric nature, having a substantially annular shape, to surround the reservoir 2.

The side wall 5 is closed both on the top and on the bottom by a pair of front walls 6, 7 preferably substantially plane, the mutual distance thereof d will vary as a function of the expansion of the side wall 5.

The height h of the wall 5 will vary as a consequence of the variation in the volume of fluid present in the reservoir 2.

Preferably, the casing 4 has a prismatic shape, with height h variable as a function of the filling-in of the reservoir 2. The volumetric increase of the casing 4 will be comprised between 100% and 300% of the original sizes with empty reservoir.

Overall, as it can be appreciated by the enclosed figures, the configuration of the device 1 preferably is polyhedral, in particular parallelepiped or box-like.

The front walls 6, 7 can be made of a third base material different from that of the side wall 5, such as a rigid or half-rigid plastic material, or the same material of the side wall 5.

Preferably, the front walls 6, 7 comprise means for the joint quick connection with the side wall 5.

In particular, in the illustrated configuration, the front walls 6, 7 comprise respective perimeter seats 8, 9 for the quick insertion of a respective edge 10, 11 of the side wall 5 and the mutual coupling therewith.

In this way the assembly of the portions is simplified, by making it however stable, and a quick and simple replacement of the side wall 5 would be allowed, if it deteriorated and the elastic properties thereof were not so as to guarantee the correct supply of fluid.

The perimeter seats 8, 9 could be constituted by both blind and through grooves, extending substantially for the whole periphery of the respective front walls 6, 7, with possible discontinuity areas.

The front walls 6, 7 are further equipped with preferably semi-circular, mutually faced and specular, recesses 12, 13, implemented in the respective edges 14, 15, placed at the opening 3 of the reservoir 2.

Figure 3:
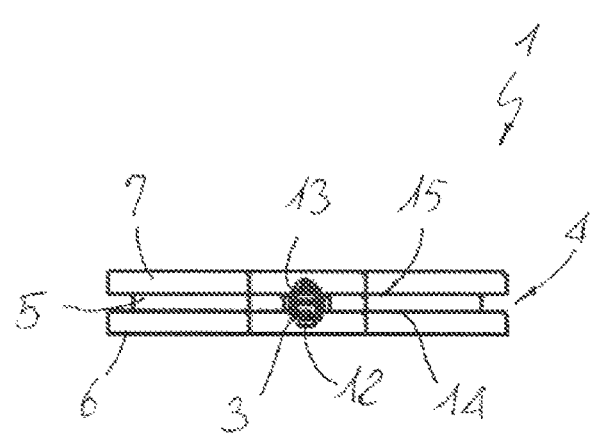
FIG. 3 is a front view of the device of FIG. 1.

In this way, in the undeformed configuration in absence of fluid, the cylindrical opening 3 of the reservoir 2 is limited in the compartment defined between the two recesses 12, 13, allowing the two front walls 6, 7 to arrive at a distance d with minimum value, by further reducing the total overall dimensions of the device, as it can be seen in FIG. 3.

According to a possible variant of the invention, the first base material of the reservoir 2 can be an elastomeric material, such as for example a silicone-based material or the like.

The first elastomeric base material not necessarily will be of the same type of the second elastomeric base material.

However, in a particular configuration, the two materials could be the same and the reservoir 2 and the side wall 5 of the casing 4 could be obtained by means of one single processing, for example an extrusion or moulding processing, to be integral therebetween and define one single body.

Advantageously, the two front walls 6, 7 will have substantially the same shape, so as to be able to be implemented with the same mould.

In this way, the device 1 according to this first variant can be implemented by moulding and by using only two moulds, according to a particularly cheap and quick processing.

Preferably, the reservoir 2 has a hollow elongated shape deriving from the deformation following the fluid entrance, with walls having a substantially constant thickness and preferably with value directly proportional to the maximum volume of fluid which can be included thereinside.

According to a preferred variant of the invention, the first base material of the reservoir 2 is a not elastically deformable material, but however flexible to allow the variation in volume after the insertion and discharge of fluid.

In this case, the first base material can be selected among the materials commonly used for the infusion bags currently on the market. In particular, the used material can be a thermoplastic material, preferably free of silicone, a non-elastomeric material. In particular, it can be in the shape of a single- or multi-layer film, comprising at least one of the following polymers: polyethylene terephthalate (PET), polyethylene (PE), high-molecular-density polyethylene (PEHD), polypropylene (PP), ethylene-vinyl acetate (EVA), polyvinyl chloride free of phtalate (PVC DHEP FREE), ultra-density polyethylene (PEUHD), Polystyrene (PS) and the like.

From an operative point of view, one proceeds with filling-in the reservoir 2, which will increase the volume thereof and will come in contact with the walls of the outer casing 4, by causing the deformation of the elastomeric portion 5 of the casing 4, which will increase its own volume too, whereas the elastomeric portion 5 will accumulate mechanical energy during the deformation thereof.

After having inserted the maximum quantity provided for the fluid and after having eliminated possible air inside the system by means of the known techniques, the device will be ready for use.

In this way, under the push exerted by the casing 4 on the reservoir 2 after the elastic return of the casing 4 to the original position, the fluid will start to outflow from the reservoir 2 and will flow into the infusion line connected thereto.

The outflow rate could be adjusted during the planning phase both by suitably selecting the materials of the reservoir 2 and of the casing 4 and by adjusting the rate outgoing from the capillary flow regulator placed downwards of the device.

In case even the reservoir 2 is made of elastomeric material, the outflow pressure will be given by the sum of the single pressures generated by the elastic return of the reservoir 2 and of the casing 4. In the preferred case of non-elastomeric reservoir 2, the push will be produced only by the casing 4.

From what described, it appears evident that the device according to the invention achieves the pre-fixed objects, in particular that of reducing the overall dimensions, above all under condition of absent fluid or lower fluid than the maximum quantity which can be included. Furthermore, it is underlined that the device advantageously provides an outer casing carrying out both a function of passive type for protecting the reservoir and an active function for the supply of fluid.

The device according to the invention can be subjected to several modifications and variants, all within the inventive concept expressed in the enclosed claims.

All details could be replaced by other technically equivalent elements, and the materials could be different according to needs, without leaving the scope of protection of the present invention.

Even if the device has been described with particular reference to the enclosed figures, the reference numbers used in the description and in the claims are used to improve the understanding of the invention and they do not constitute any limitation to the claimed protection scope.

The present invention has been so far described with reference to preferred embodiments. It will be appreciated that other embodiments belonging to the same inventive idea may exist, as defined by the scope of protection of the claims set forth below.

The invention claimed is:

1. A device for infusion of fluids, comprising:
an internal reservoir for a fluid to be administered made of a first flexible base material to vary its volume as a function of the quantity of fluid present thereinside, said first base material being a non-elastomeric thermoplastic material, said reservoir being fluidically connectable to an infusion line adapted for administering the fluid; and
an outer casing containing said reservoir, wherein said outer casing comprises
a side wall made of a second, elastic base material, suitable to make elastically deformable said casing to vary the geometry and internal volume thereof as a function of the volume of said reservoir, and
a pair of front walls respectively made of a third rigid or semi-rigid base material, wherein a first front wall of said pair is positioned on top of the side wall and a second front wall of said pair is positioned on bottom of the side wall,
wherein said side wall and said pair of front walls together surround said reservoir in a manner such that said reservoir is not exposed to an outer environment except through said infusion line,
wherein said reservoir has an opening adapted to be placed selectively in fluidic communication with said infusion line to allow both the introduction of the fluid thereinside and the administration of the fluid at the outside,
wherein each one of said front walls has a recess, said recesses being mutually mirrored structures about a shared plane, implemented at said opening, and configured so that in a configuration of minimum overall dimensions of said device said opening is surrounded in a compartment defined by said recesses,
the configuration being such that
the filling-in with the fluid causes an increase in volume of said internal reservoir, which, in turn, causes an increase in volume of said outer casing and
correspondingly, after the fluid administration, the volume of said outer casing, and thus the volume of the device, decreases proportionally to the volume of supplied fluid.

2. The device according to claim 1, wherein said front walls comprise respective joint elements for connecting to said side wall.

3. The device according to claim 1, wherein said front walls comprise respective perimeter seats for the insertion of a respective edge of said side wall and the mutual coupling therewith.

4. The device according to claim 1, wherein said first base material of said reservoir is free of silicone materials.

5. The device according to claim 1, wherein said first base material of said reservoir is selected from the group consisting of: polyethylene terephthalate (PET), polyethylene (PE), high-molecular-density polyethylene (PEHD), polypropylene (PP), ethylene-vinyl acetate(EVA), polyvinyl chloride free of phtalate (PVC DHEP FREE), ultra-density polyethylene (PEUHD), Polystyrene (PS) and the like.

6. The device according to claim 1, having an overall polyhedral, in particular parallelepiped or box-like configuration.

7. The device according to claim 1, wherein said reservoir is divided into two or more sections, optionally independent therebetween, connected to the same infusion line.

* * * * *